United States Patent
Campbell et al.

(10) Patent No.: US 10,473,586 B2
(45) Date of Patent: Nov. 12, 2019

(54) ENHANCED OPTICAL DATA CAPTURE USING NDIR FOR LIQUIDS

(71) Applicant: Airware, Inc., Goleta, CA (US)

(72) Inventors: Thomas Campbell, Newbury Park, CA (US); Jacob Y Wong, Goleta, CA (US)

(73) Assignee: AIRWARE, INC., Goleda, CA (US)

( * ) Notice: Subject to any disclaimer, the term of this patent is extended or adjusted under 35 U.S.C. 154(b) by 0 days.

(21) Appl. No.: 16/359,350

(22) Filed: Mar. 20, 2019

(65) Prior Publication Data

US 2019/0219500 A1 Jul. 18, 2019

Related U.S. Application Data

(63) Continuation-in-part of application No. 16/056,531, filed on Aug. 7, 2018, now Pat. No. 10,241,044, which is a continuation-in-part of application No. 15/785,829, filed on Oct. 17, 2017, now Pat. No. 10,041,881, which is a continuation-in-part of application No. 15/644,775, filed on Jul. 8, 2017, now Pat. No. 9,823,185, which is a continuation-in-part of application No. 15/594,418, filed on May 12, 2017, now Pat. No. 9,726,601, which is a continuation-in-part of application No. 15/444,136, filed on Feb. 27, 2017, now Pat. No. 9,678,000, which is a continuation-in-part of application No. 15/358,873, filed on Nov. 22, 2016, now Pat. No. 9,606,053.

(51) Int. Cl.
| | | |
|---|---|---|
| *G01N 21/59* | (2006.01) | |
| *G01N 33/49* | (2006.01) | |
| *G01N 21/35* | (2014.01) | |
| *G01N 21/27* | (2006.01) | |
| *G01J 3/42* | (2006.01) | |
| *G01N 21/3577* | (2014.01) | |

(52) U.S. Cl.
CPC ........ *G01N 21/3577* (2013.01); *G01N 33/49* (2013.01); *G01N 2201/127* (2013.01)

(58) Field of Classification Search
CPC ... G01J 3/427; G01N 21/274; G01N 21/3577; G01N 21/59; G01N 33/49; G01N 2021/3148; G01N 2021/473; G01N 2201/0696; G01N 2201/127
See application file for complete search history.

(56) References Cited

U.S. PATENT DOCUMENTS

| | | | |
|---|---|---|---|
| 6,509,567 B2 * | 1/2003 | Boudet | G01M 3/002 250/343 |
| 2005/0012042 A1 * | 1/2005 | Weckstrom | G01N 21/3504 250/343 |
| 2017/0265787 A1 | 9/2017 | Wong | |

* cited by examiner

*Primary Examiner* — Mark R Gaworecki
(74) *Attorney, Agent, or Firm* — Roy L. Anderson

(57) ABSTRACT

The concentration of a targeted molecule (such as glucose) in a liquid medium having at least one interfering molecule coexisting with the targeted molecule is detected by use of NDIR and a sampling technique in which an imposed location of a pulse beam from a signal source, an interference source and a reference source is varied over a plurality of sites of a sampling area.

11 Claims, 13 Drawing Sheets

ENHANCED OPTICAL DATA CAPTURE USING NDIR FOR LIQUIDS

CROSS-REFERENCE TO RELATED APPLICATIONS

The present invention is a continuation-in-part application of U.S. Ser. No. 16/056,531, filed Aug. 7, 2018, which is a continuation-in-part of U.S. Ser. No. 15/785,829 filed Oct. 17, 2017, which was issued on Aug. 7, 2018 as U.S. Pat. No. 10,041,881, which is a continuation-in-part of U.S. Ser. No. 15/644,775 filed Jul. 8, 2017, which was issued on Nov. 21, 2017 as U.S. Pat. No. 9,823,185, which is a continuation in part of U.S. Ser. No. 15/594,418 filed May 12, 2017, which was issued on Aug. 8, 2017 as U.S. Pat. No. 9,726,601, which is a continuation-in-part application of U.S. Ser. No. 15/444,136 filed Feb. 27, 2017, which was issued on Jun. 13, 2017 as U.S. Pat. No. 9,678,000, which is a continuation-in-part application of U.S. Ser. No. 15/358,873, filed Nov. 22, 2016, which was issued on Mar. 28, 2017 as U.S. Pat. No. 9,606,053, the disclosures of all of which are specifically incorporated herein by reference.

FIELD OF THE INVENTION

The present invention relates to an improved Non-Dispersive Infra-Red (NDIR) absorption method to detect molecules in the liquid phase.

BACKGROUND OF THE INVENTION

Non-Dispersive Infra-Red (NDIR) is a common and excellent measurement technique for detecting gases in the atmosphere. NDIR sensors utilize the principle that various gas molecules exhibit substantial absorption at specific wavelengths in the infrared radiation spectrum. The term "non-dispersive" as used herein refers to the apparatus used, typically a narrow-band optical or infrared transmission filter, instead of a dispersive element such as a prism or diffraction grating. The optical filter isolates the radiation in a particular wavelength band that coincides with a strong absorption band of a gas species for the purpose of said gas species measurement.

The present invention builds upon past inventions disclosed in related applications to further advance use of NDIR to detect molecules in a liquid medium.

This and further objects and advantages will be apparent to those skilled in the art in connection with the figures and the detailed description of the invention set forth below.

SUMMARY OF THE INVENTION

The present invention is generally directed to a process and apparatus useful for determining a concentration of a targeted molecule M (such as glucose) within a given time period in a liquid sampling matrix in which at least one interfering molecule $M_I$ coexists with the targeted molecule. A multiplexer and a collimator are configured to pulse infrared radiation from a signal source, an interference source and a reference source into a pulsed beam which is directed at a first inclined angle $(\theta_{i1})$ to a normal of a first spot of the liquid sampling matrix. A detector is configured to detect infrared radiation after it emerges from the first spot as a first pulsed signal and reference channel output and a first pulsed interference signal and reference channel output from the pulsed beam after it penetrates into the spot. The imposed location of the pulsed beam is changed so that it is directed at a second inclined angle $(\theta_{i2})$ to a normal of a second spot of the liquid sampling matrix and the detector is configured to detect infrared radiation after it emerges from the second spot as a second pulsed signal and reference channel output and a second pulsed interference signal and reference channel output from the pulsed beam after it penetrates into the second spot. The imposed location of the pulsed beam can be changed without changing the physical location of either the pulsed beam or the detector by use of an optical device which itself can be moved by a piezo/electronic, electronic, magnetic or mechanical means; alternatively, the physical location of the pulsed beam and/or the detector can be changed. Signal processing is provided for: (1) obtaining a first average ratio value of $R_{-ave}(t_1)$ for a first preselected period of time ("$t_1$") from the first pulsed signal and reference channel output, where $R_{ave}(t_1)$=signal channel/reference channel output for the first preselected period of time; (2) obtaining a first average ratio value of $R_{Jave}(t_2)$ for a second preselected period of time ("$t_2$") from the first pulsed interference and reference channel output, where $R_{Jave}(t_2)$=interference channel/reference channel output for the second preselected period of time; (3) obtaining a second average ratio value of $R_{ave}(t_3)$ for a third preselected period of time ("$t_3$") from the second pulsed signal and reference channel output, where $R_{ave}(t_3)$=signal channel/reference channel output for the third preselected period of time; and (4) obtaining a second average ratio value of $R_{Jave}(t_4)$ for a fourth preselected period of time ("$t_4$") from the second pulsed interference and reference channel output, where $R_{Jave}(t_4)$=interference channel/reference channel output for the fourth preselected period of time. Electronics are configured to use $R_{Jave}(t_2)$ and $R_{Jave}(t_4)$ to determine that a calibration curve is valid for the given time period and, if the calibration curve is valid, to calculate the concentration of the targeted molecule M in the liquid sampling matrix by use of $R_{ave}(t_1)$, $R_{ave}(t_3)$ and the calibration curve and provide the concentration of the targeted molecule M in the liquid sampling matrix as an output.

The object of the present invention is to provide an improved system and process for detection of molecules in a liquid medium using NDIR and a sampling technique in which an imposed location of a pulse beam is varied.

This and further objects and advantages will be apparent to those skilled in the art in connection with the figures and the detailed description of the invention set forth below.

DETAILED DESCRIPTION OF THE INVENTION

Figure 1:
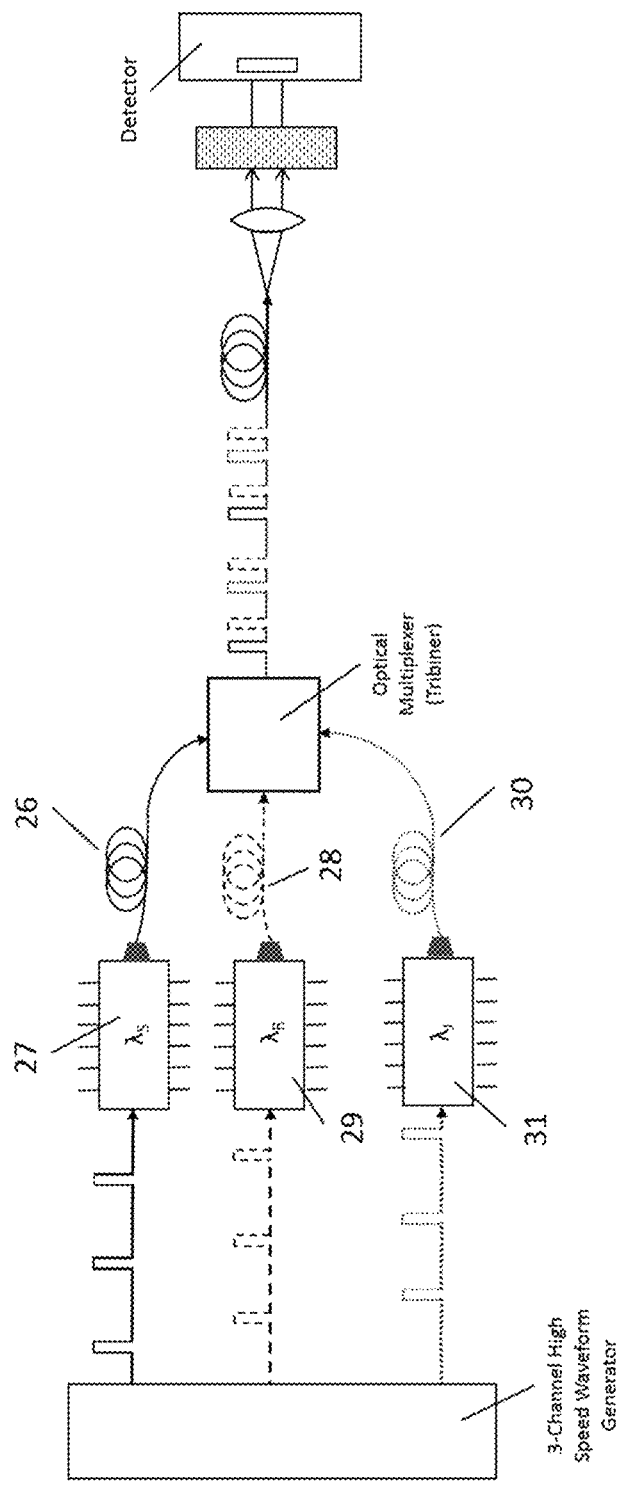
FIG. 1 illustrates an optical setup illustrating how a Signal diode laser, a Reference diode laser and an Interference diode laser are driven alternatively and successively by a 3-channel high speed waveform generator.

U.S. Pat. No. 9,606,053 (2017) discloses an NDIR method which significantly suppresses scattering noise attributable to the much higher molecular density which is encountered in a liquid medium, as opposed to a gaseous medium. The method utilizes alternating and successively pulsing infrared radiation from signal and reference sources which are multiplexed and collimated into a single pulsed beam directed through the liquid sample. The pulse frequency is set sufficiently fast so as to provide almost the same molecular configuration to both the signal and the reference beams. The scattering noise encountered by both beams is effectively the same and can be significantly reduced through processing the ratio of their respective pass-through outputs.

U.S. Pat. No. 9,678,000 (2017) discloses using an NDIR method to detect glucose in a liquid medium. Glucose has an overtone absorption band located at 1,150 nm which can be used as the center wavelength for the signal beam. This absorption band is desirable because it has a water absorption coefficient of no greater than ~1.0 cm$^{-1}$, which is especially preferred, as it helps to minimize effects created by water absorption. A reference beam wavelength of 1,064 nm, where there is no glucose molecule absorption, can be used as the center wavelength for the reference beam.

U.S. Pat. No. 9,726,601 (2017) discloses an improved NDIR method for determining the concentration of targeted molecules labeled M in a liquid medium admixed with interfering molecules labeled $M_J$ which uses an additional interference radiation source besides those of the signal and reference to significantly reduce the interference noise. U.S. Pat. No. 9,823,185 (2017) discloses an improvement to this method with suppression of both scattering and absorption interference noise (AIN) via a reflection detection technique.

The present invention utilizes a signal source, an interference source, a reference source, a multiplexer and a collimator to pulse radiation in a pulsed beam which is detected by a detector as is described in greater detail in U.S. Pat. Nos. 9,606,053 and 9,823,185. The signal source emits radiation at a signal wavelength which is within a first absorption band of the targeted molecule M, the interference source emits radiation at an interference wavelength which is within a second absorption band of said at least one interfering molecule $M_J$, and the reference beam emits radiation at a reference wavelength which is neutral and is not within either the first absorption band or the second absorption band; at least one interfering molecule $M_J$ absorbs radiation at the signal wavelength; and the signal source, the interference source and the reference source are each pulsed at a preselected frequency of at least N Hz which is sufficiently fast so that a given molecule of the targeted molecule M or said at least one interfering molecule $M_J$ will not pass in and out of the liquid sampling matrix within the preselected frequency.

Figure 8:
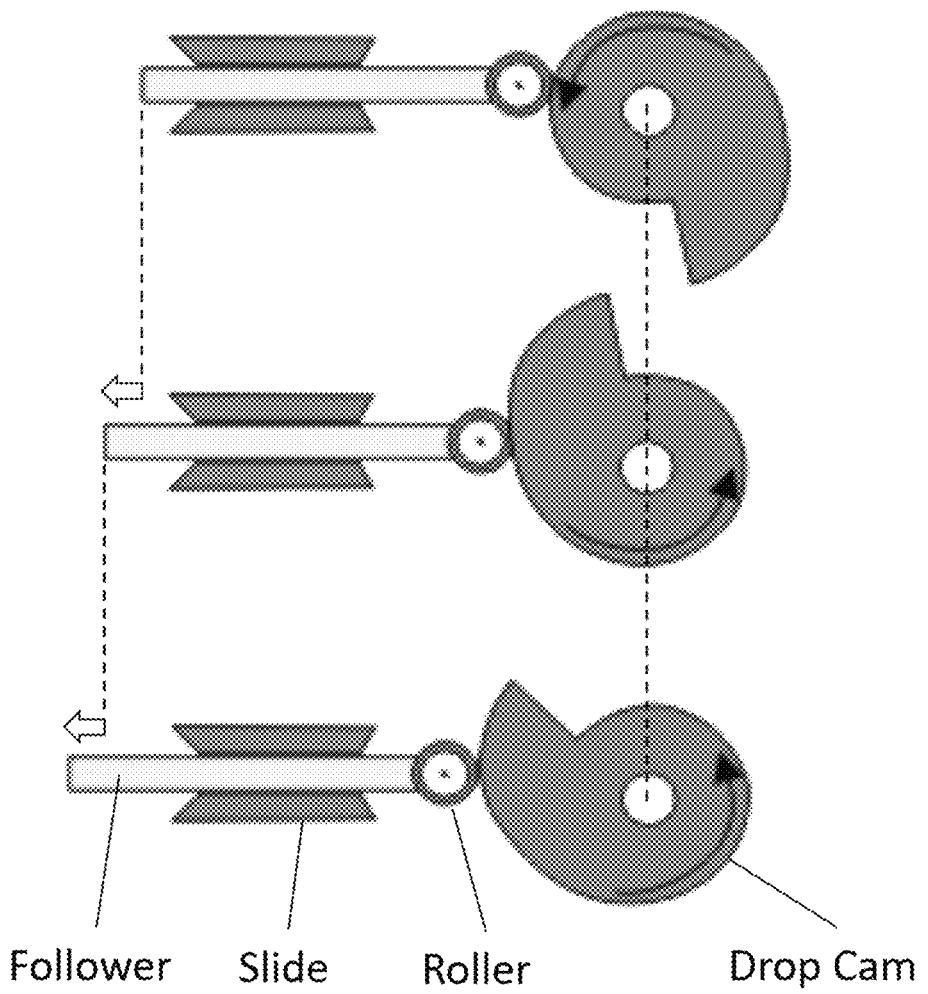

FIG. 1 (which is FIG. 8 in U.S. Pat. No. 9,823,185) illustrates an optical setup of a Signal diode laser, a Reference diode laser and an Interference diode laser which are driven alternately and successively in groups of two by a 3-channel high speed waveform generator. As shown in FIG. 1, output 26 of Signal diode laser 27 is driven alternately and successively with output 28 of Reference diode laser 29 as a pair; meanwhile output 30 of Interference diode laser 31 is driven alternately and successively with output 28 of Reference diode laser 29 as another pair. The rest of the optical and electronic processing system setup for a three-diode laser system to suppress both scattering noise and AIN is the same as the two-diode laser system disclosed in U.S. Pat. No. 9,606,053 (2017) for suppressing just the scattering noise.

U.S. Pat. No. 10,041,881 (2018) discloses an improved NDIR method for liquids in which scattering noise is reduced and an Absorption Interference Noise (AIN) is suppressed with a reflection technique.

U.S. Ser. No. 16/056,531 discloses a process for deciding the validity of the calibration curve for targeted molecules $M_G$ in a liquid sample with interfering molecules. This value can further be used to adjust the calibration curve via a parameter linking the transmittances measured at the signal and interference wavelength channels in order to assure its validity.

A potential limitation of the techniques described in our earlier patents for optical sensing in liquids is a very small sample volume per measurement. In order to enhance the accuracy, precision and reliability of measurements with our inventive Direct Infrared Laser Absorptive Scattering Technique (DILAST) sensors, the present invention incorporates different sample capture techniques.

DILAST optical sensing for liquids can be applied to containerized samples, fluid flows, semi-solid materials, and solid materials all of which have optical permeability such that optical wavelengths can penetrate to some level that allows absorption of target elements or compounds so that detector measurements can be made of said absorption. For the embodiment of sensing in human tissue, which for the purpose of the present invention will be defined as being a liquid medium which has a dynamic volume with considerable molecular motion incorporating a non-homogenous structure. Many elements and compounds comprise skin with arrangements according to their functions. Knowing that DILAST sensor systems have to work with these complex samples, the present invention sets forth several methods for improving optical sensor data capture from such samples.

Of the various elements affecting optical absorption in skin, water is the primary absorber by volume. Accounting for hydration of the skin is necessary for highest detection accuracy of glucose in interstitial fluid. Next are various lipids including adipose tissue in skin, followed by melanin in the epidermis, then white blood cells and red blood cells (oxygenated and de-oxygenated) in arteries, veins, and capillaries. Lastly, we step down in volume to proteins, and glucose.

Figure 6:
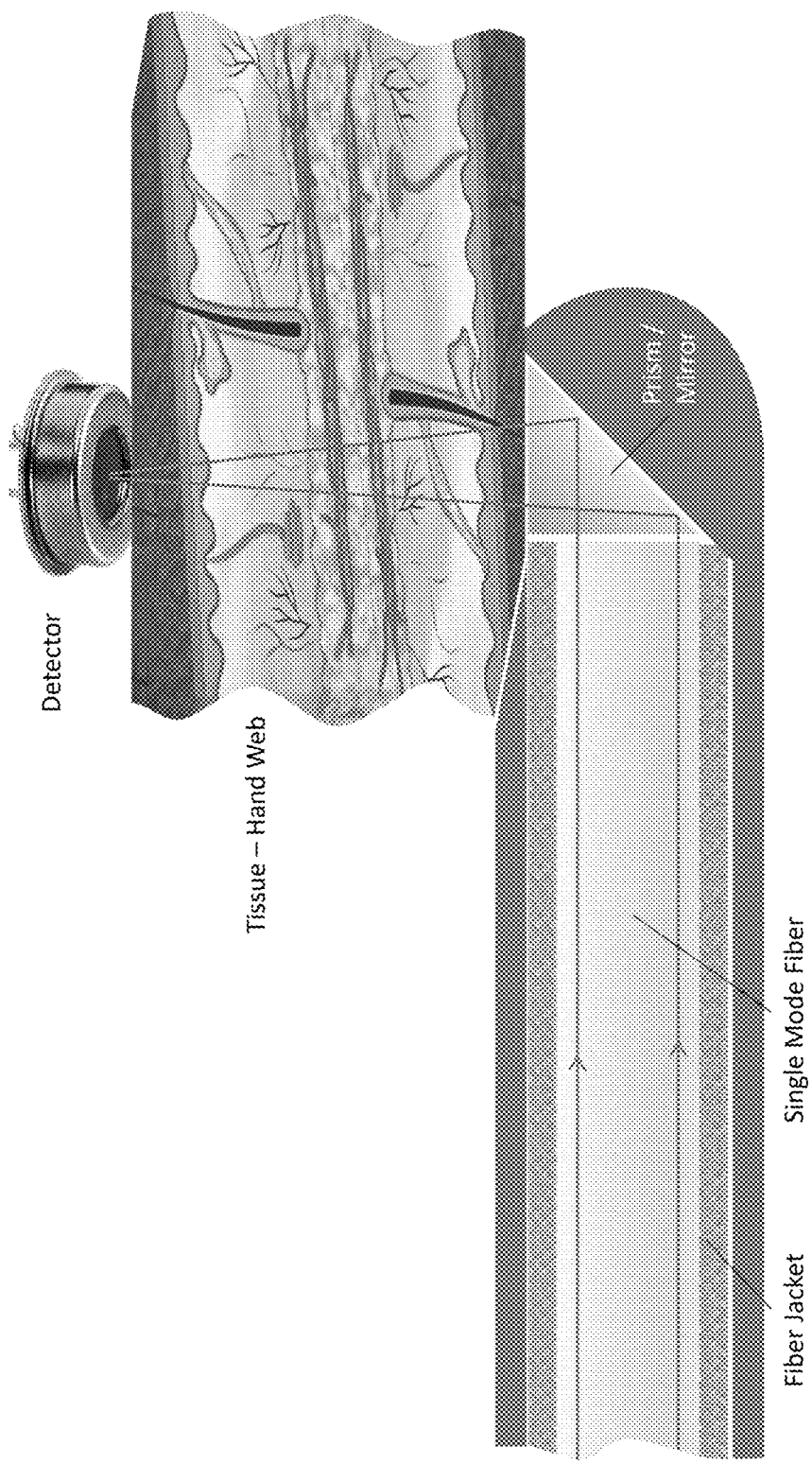
FIG. 6 illustrates a pulsed beam according to the present invention being delivered by way of a single mode optical fiber to a prism or mirror such that the profile is kept low and the controlled light beam can enter the specimen or media

Minimization of the total optical energy imposed on skin is important to the functioning of the DILAST technique. Very specific reference and target species wavelengths are employed to accomplish scattering noise cancellation technique according to the present invention. And beyond the controlled wavelengths, the present invention employs a "relatively" small "beam" of optical energy whose resulting scattering and absorption effects are captured on "relatively" small detectors as shown in one configuration described by FIG. 6.

As data manipulation techniques improve with time, one may be able to employ larger beams and be able to process out the larger noise factors. With larger beams, one naturally captures a large sample volume which promotes the goal of high accuracy, precision, and reliability of measurements. However, if one is using a "relatively" small beam, one needs to, in some fashion, scan this beam across a "sample" such that one truly captures a representative data set of the non-homogenous "sample,' and such scanning can be linear, circular, or some combination or hybrid motion such that during the set measurement time, a "comprehensive" data set is captured for calculating values and averaging those values across said "comprehensive" data set. If the samples obtained are not of constant volume, it is especially preferred that non-constant volume illumination must be addressed in the analysis of the data captured to correct for the effects of either larger or smaller "illumination volumes".

Mechanics of the scanning motion according to the present invention can be implemented with a linear, circular, or combination of linear and circular that best includes a suitable sample volume and subsequent suitable data set, and methods for linear, circular, or hybrid travel can be implemented with electronic, magnetic, or pressure forces. The goal with implementation is smallest size and cost to accomplish the necessary range of motion for a suitable set of scan sites.

Figure 7:
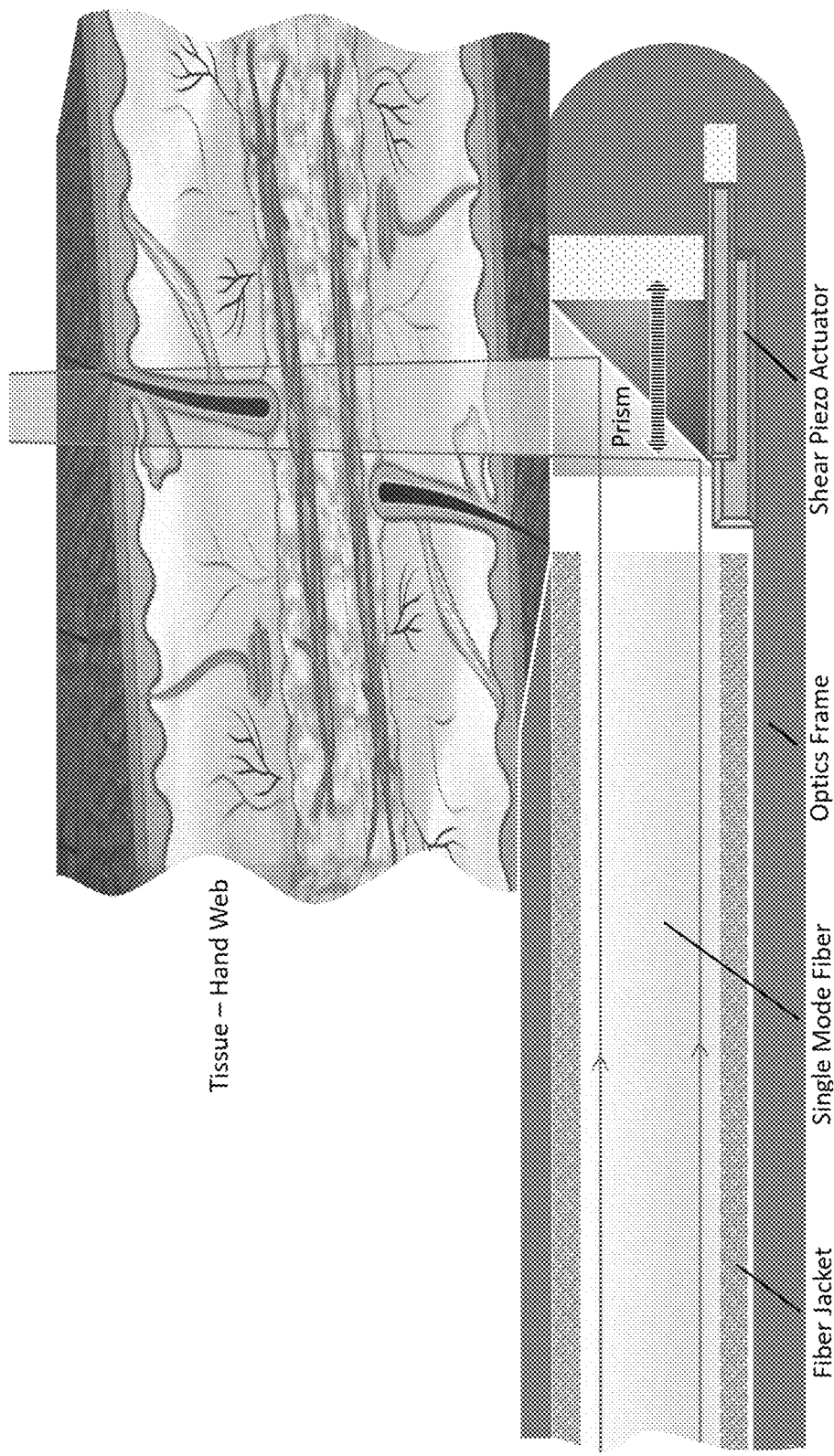
FIG. 7 illustrates the concept of using rotational motion to create a linear scan path by implementation of a rotary drop cam system illustrated in FIG. 8.

One preferred embodiment for implementing scanning motion according to the present invention is to employ a piezo linear or rotary motor which offers high precision and repeatable positioning. There are many other motor elements that can be employed as well. FIG. 7 represents one implementation of a linear motor moving a mirror in a back and forth motion to obtain a linear scan pattern such that the scan sites are identical in volume. FIG. 8 represents the implementation of a rotary motion source to create a linear motion that likewise can move a mirror for stepping a beam across more than one scan sites.

The next step is choosing whether to apply the motion to just the emitter and/or emitter beam and scan across the detector or move the emitter and detector in tandem. The first requires that the detector area is suitable large as to capture data as the emitter and/or emitter beam travels. The second option allows the detector area to remain small and cost-effective, but implementing the tandem travel of the emitter and the detector is more complex.

One embodiment of scanning can be accomplished with a small linear actuator moving a mirror element such that the emitter beam is scanned across multiple sample sites on the test sample or specimen.

Figure 9:
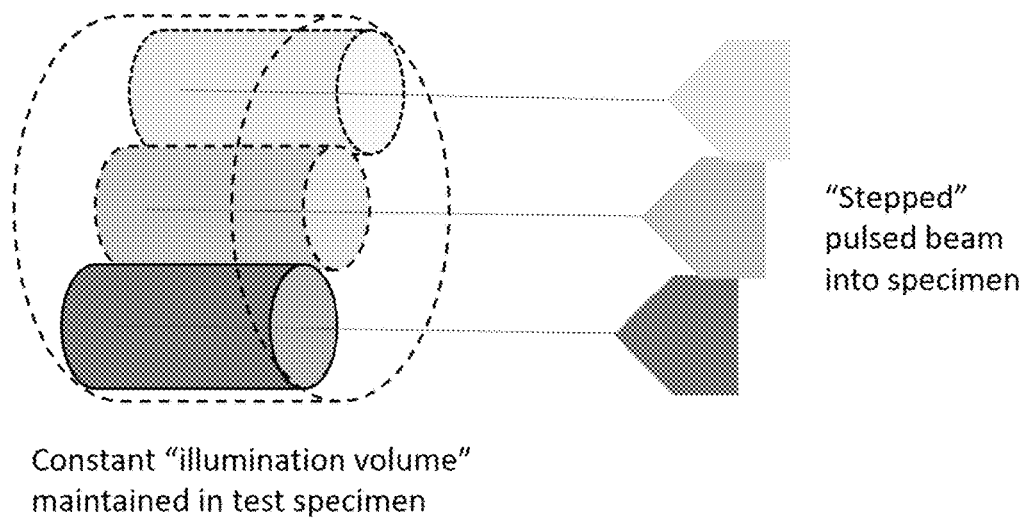
FIG. 9 Illustrates multiple scan sites with a linear scan pattern where each separate scan site comprises a constant volume for equivalent and optimum data capture and comparison analysis.

A shear piezo actuator can linearly move a prism and beam across a scan zone. This scan zone portrayed in FIG. 9 is limited to the available detector area. Multiple sample sites are illuminated for some typical dwell time at each of the three sites in or on the tissue. As noted, the detector area must be sufficiently large to capture reflected and transmitted optical signals. With this technique, a more comprehensive sample is obtained of the tissue that includes interstitial fluid, tissue types, veins, capillaries, follicles, nerves, etc.

Figure 10:
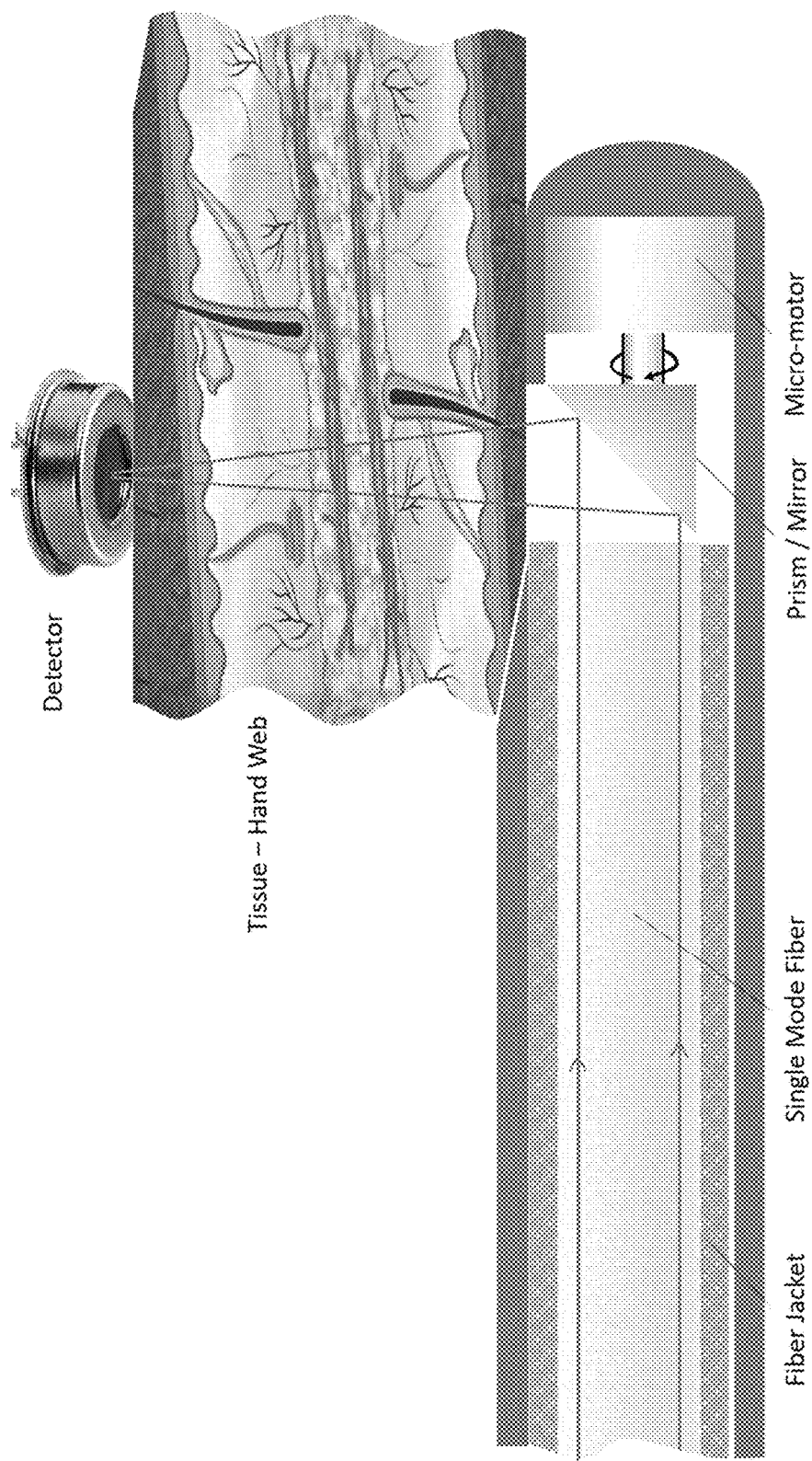
FIG. 10 t illustrates one possible method of using rotational motion to establish a scan range of the specimen or media under test by use of a rotating actuator a mirror or some element to redirect the pulsed beam in a precise and consistent fashion.

Another embodiment shown in FIG. 10 uses a rotary element to step the mirror element such that the single beam is directed onto the detector through separate pathways through the sample.

With a goal of ideal optical data capture from skin, one embodiment incorporates three or more illumination locations in the skin by simply moving the light beam and not the detector. The optics to move the light beam are smaller and more precise than moving the detector housing. The detector will require a sufficient surface area to receive energy from each of the scan sites. The use of a mirror should retain properties of the light beam better than a lens system. The actuator choice for moving the mirror should be precise, repeatable, small, and low power.

Figure 11:
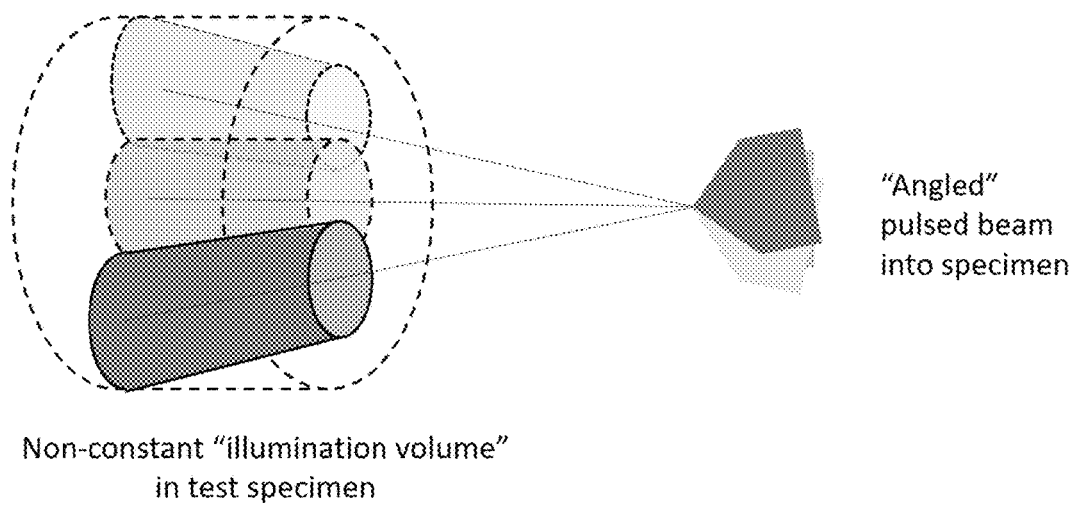
FIG. 11 demonstrates that adding any angularity to the progressive scanning method creates slightly different volumes illuminated in the specimen or media under test.

The scan zone portrayed in FIG. 11 is likewise limited to the available detector area, however, the scan volumes resulting from the angled beams are slightly different. Therefore, the "detected" results must be interpreted to allow for the slightly different reflection, absorption, transmission, and scattering results captured.

Figure 12:
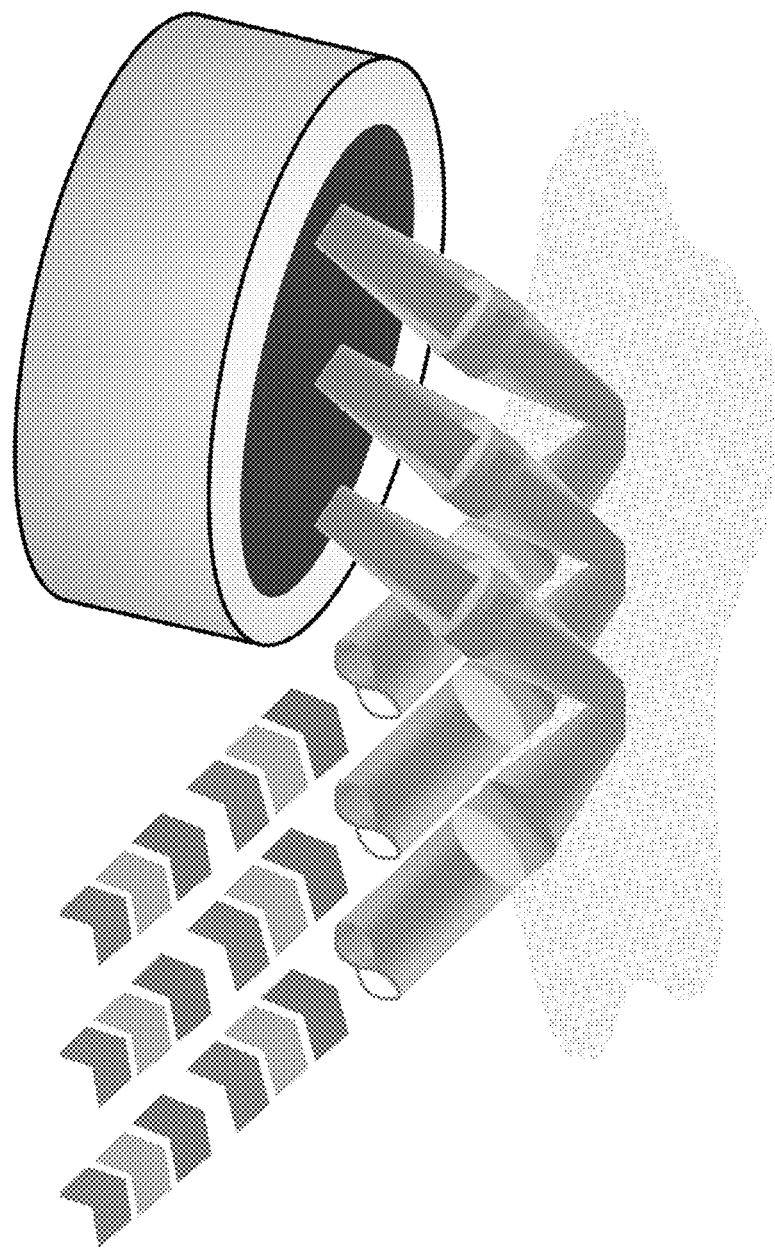
FIG. 12 illustrates using the pulsed beam in accordance with the present invention in a reflective approach to the specimen or media under test. Portrayed is a linear scan step pattern such that each illumination site is identical in illumination area leading to near-identical data capture at the detector.
Figure 13:
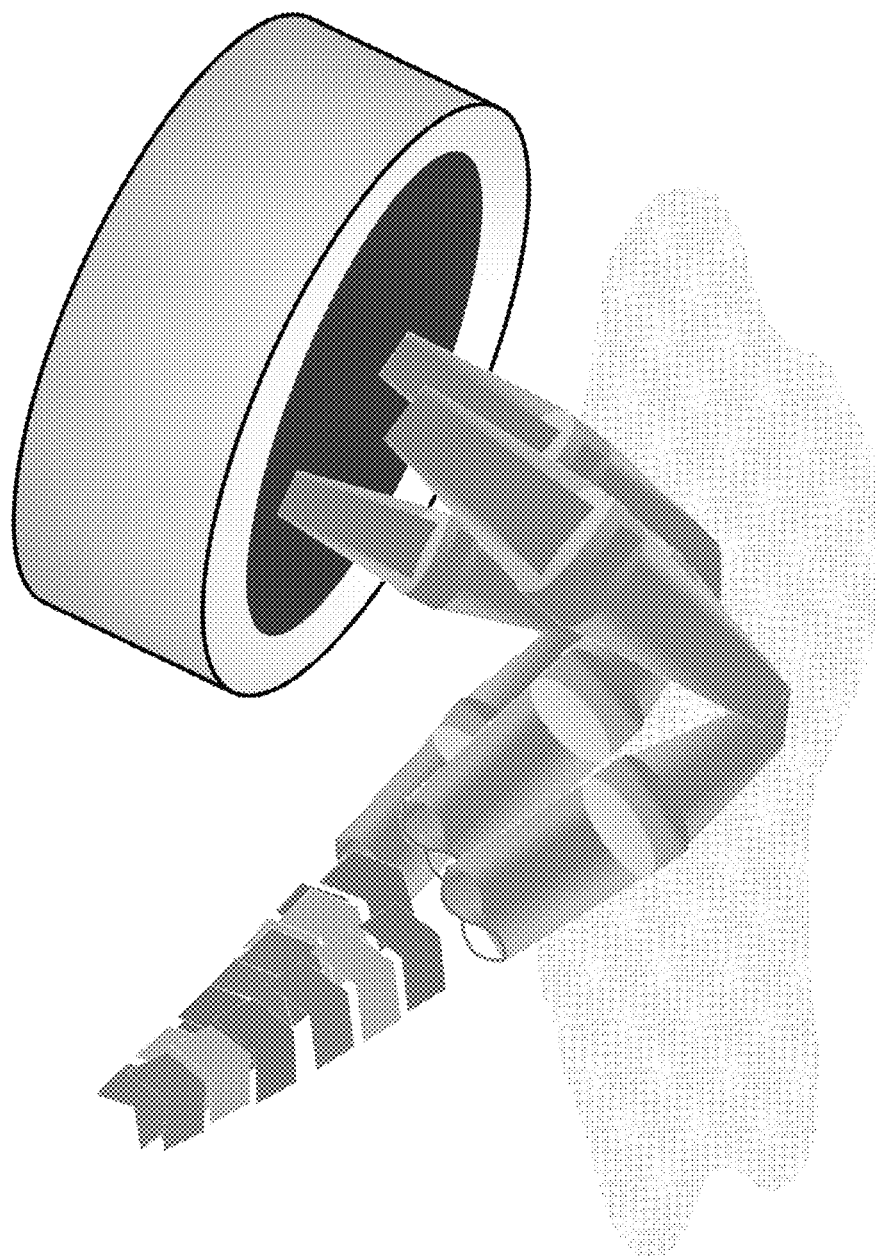
FIG. 13 is another proposed reflective scanning pattern where the illuminating beam is angled in order to gather data from two or more scan sites. The angled beams create slightly different scan site areas (such that the data collected at the detector must be adjusted to account for these variations.)

An import aspect of the inventive optical detection method is the application can be in both a transmissive approach as well as a reflective approach. Employing a reflective illumination data gathering method increases options for scanning configurations. With respect to the human body, transmission scanning is limited to certain accessible areas on the body such as the handweb, earlobe, nostril, cheek, eyelid, or fingers and toes, whereas reflective scanning expands typical locations on the human body to include the wrist, upper arm, abdomen, lower back, thigh, and calf as to where a sensor can be attached or worn for both spot and continuous monitoring. FIGS. 12 and 13 illustrate using the pulsed beam in accordance with the present invention in a reflective approach to the specimen or media under test. Both linear scan steps as well as angular scan patterns can be exercised for reflective data collection. As noted, with linear scan stepping, each illumination site is identical in illumination area leading to near-identical data capture at the detector as in FIG. 12. Another proposed reflective scanning pattern where the illuminating beam is angled in order to gather data from two or more scan sites is portrayed in FIG. 13. The angled beams create slightly different scan site areas (such that the data collected at the detector must be adjusted to account for these variations.)

The following is a set of parameters of the scanning pattern and hardware for especially preferred embodiments of the present embodiment: Range of motion: 1-3 mm with step-and-settle times plan of <1 ms to <1 second (depending on data capture); Pattern of motion: linear or arc, linear precision <0.01 mm or angular precision of <1 mrad; System volume: small as possible; Actuation: piezo-linear or motor-rotary; Very low power, battery operated; Ability to return to set position and hold; Robustness for surviving temperature, shock, and humidity in field use; Embedded controller for ease of system integration.

Each "scan column" with the time-based narrow band spectroscopy sees a matrix of skin components. By moving the "scan column", data capture ensures a comprehensive inclusion of more skin conditions yielding better averaged values of glucose in interstitial fluid for each measurement "set."

One option of creating this emitter housing is with photo-definable glass-ceramics, machining of a metal or plastic, or by injection molding the housing.

Figure 2:
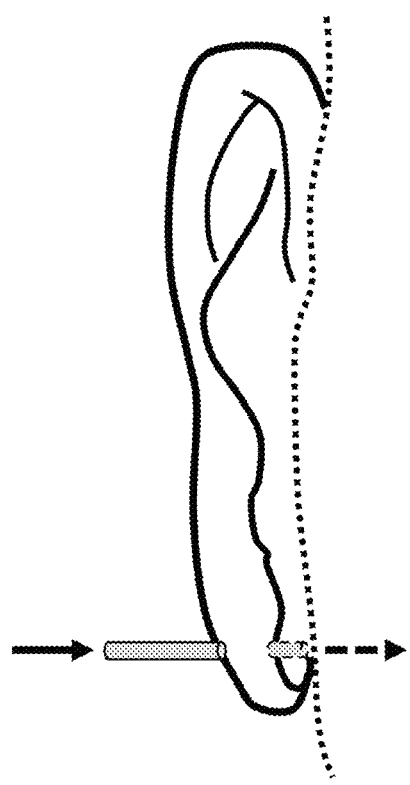
FIG. 2 is a side view which illustrates a pulsed beam as it passes through a liquid medium of an earlobe.
Figure 3:
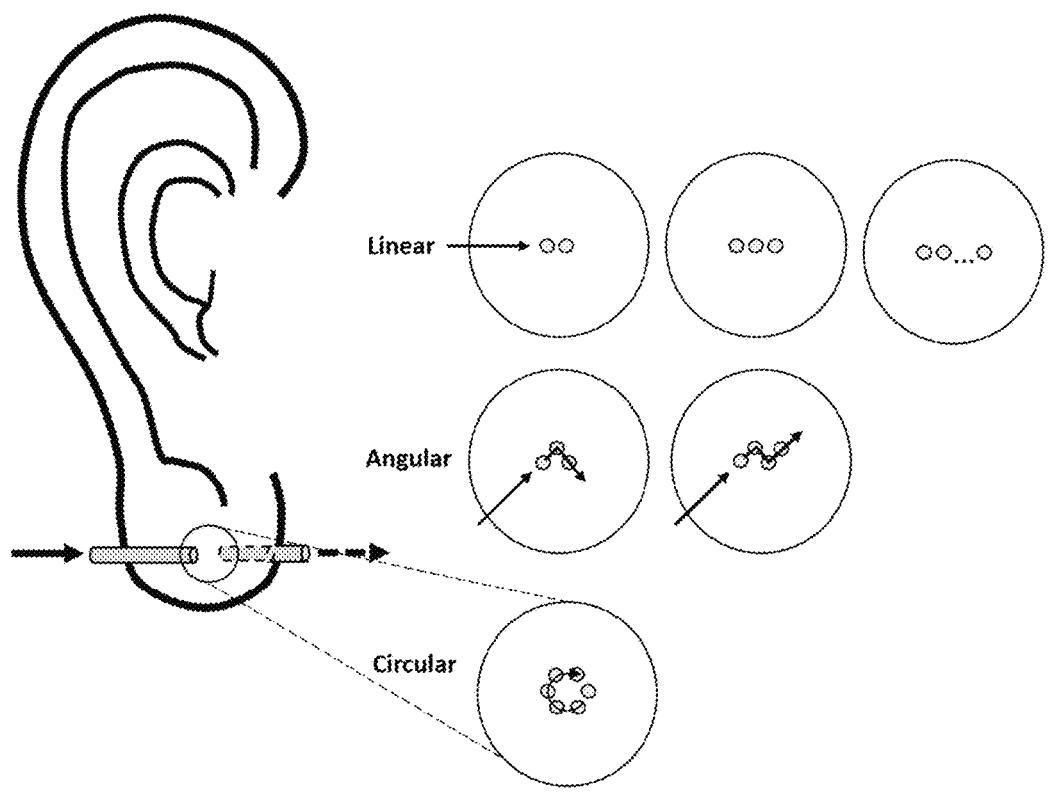
FIG. 3 is a front view of FIG. 2 and includes details of six different spot patterns for three options of multi-site scanning patterns: linear, non-linear, and circular.
Figure 4:
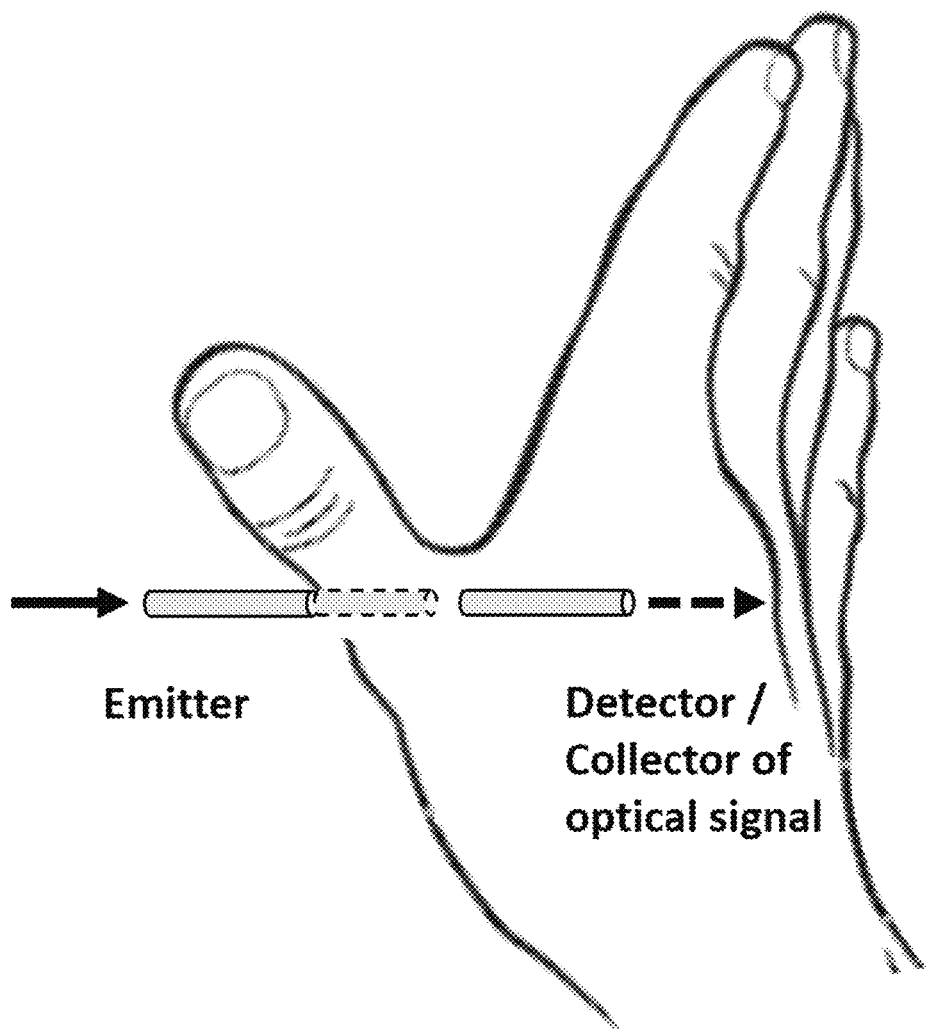
FIG. 4 illustrates a pulsed beam as it passes through a liquid medium of a handweb.
Figure 5:
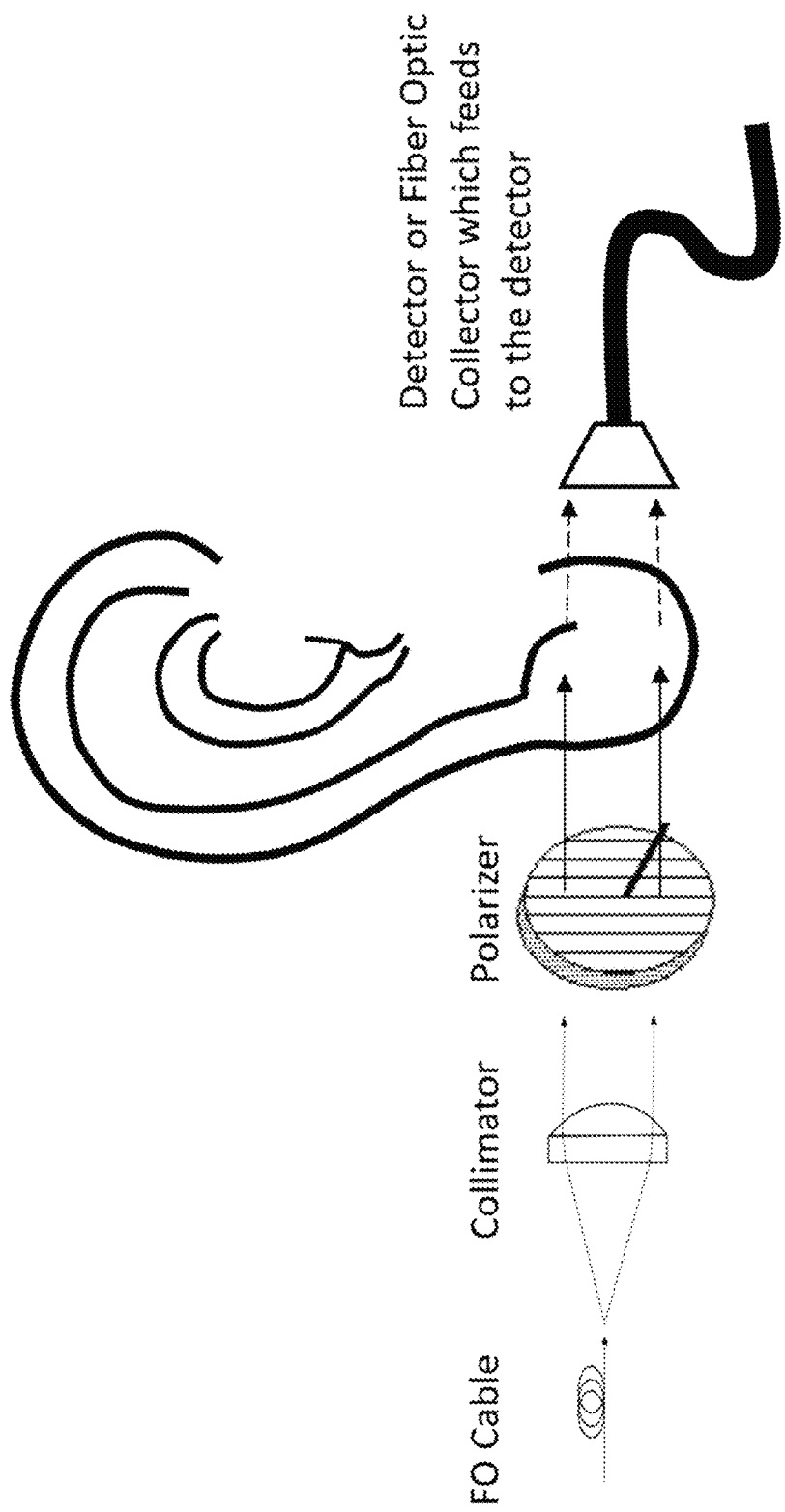
FIG. 5 illustrates a concept showing how polarized light is collected to feed a detector and incorporated into the present invention.

The inventive concepts already described herein can be applied to a wearable device using a reflection technique or be used in a device that can, in essence, be clipped on to a suitable portion of the human body, examples of which include a handweb or earlobe, which are illustrated in FIGS. 2 and 4, respectively. If a clip-on type device is desired, it may be beneficial to also use a fiber optic collector, or some other collection device, which serves to make the skin clamp device smaller and lighter, may enable increasing the sample collection area and may serve to concentrate the collected optical data allowing use of a smaller detector element. It might also be desirable to use polarized light because it may enhance absorption by glucose molecules and/or it may help to prevent absorption by other compounds in skin. Different types of light polarization might be implemented to achieve optimum absorption and minimized scattering, so linear and/or circular polarization might enhance overall accuracy, precision, and reliability of target species measurement.

While the invention described herein with reference to certain preferred embodiments, these embodiments have been presented by way of example only, and not to limit the scope of the invention. Additional embodiments thereof will be obvious to those skilled in the art having the benefit of this detailed description. Further modifications are also possible in alternative embodiments without departing from the inventive concept.

What is claimed is:

1. An apparatus for determining a concentration of a targeted molecule M within a given time period in a liquid sampling matrix in which at least one interfering molecule $M_J$ coexists with the targeted molecule, comprising:
   a signal source;
   an interference source;
   a reference source;
   a multiplexer and a collimator configured to pulse infrared radiation from the signal source, the interference source and the reference source into a pulsed beam which is directed at a first inclined angle ($\theta_{i1}$) to a normal of a first spot of the liquid sampling matrix;
   a detector configured to detect infrared radiation after it emerges from the first spot as a first pulsed signal and reference channel output and a first pulsed interference signal and reference channel output from the pulsed beam after it penetrates into the first spot;
   means for changing the imposed location of the pulsed beam so that it is directed at a second inclined angle ($\theta_{i2}$) to a normal of a second spot of the liquid sampling matrix and the detector is configured to detect infrared radiation after it emerges from the second spot as a second pulsed signal and reference channel output and a second pulsed interference signal and reference channel output from the pulsed beam after it penetrates into the second spot;
   signal processing for:
   obtaining a first average ratio value of $R_{ave}(t_1)$ for a first preselected period of time ("$t_1$") from the first pulsed signal and reference channel output, where $R_{ave}(t_1)$ =signal channel/reference channel output for the first preselected period of time;
   obtaining a first average ratio value of $R_{Jave}(t_2)$ for a second preselected period of time ("$t_2$") from the first pulsed interference and reference channel output, where $R_{Jave}(t_2)$=interference channel/reference channel output for the second preselected period of time;
   obtaining a second average ratio value of $R_{ave}(t_3)$ for a third preselected period of time ("$t_3$") from the second pulsed signal and reference channel output, where $R_{ave}(t_3)$=signal channel/reference channel output for the third preselected period of time, and
   obtaining a second average ratio value of $R_{Jave}(t_4)$ for a fourth preselected period of time ("$t_4$") from the second pulsed interference and reference channel output, where $R_{Jave}(t_4)$=interference channel/reference channel output for the fourth preselected period of time; and
   electronics configured to use $R_{Jave}(t_2)$ and $R_{Jave}(t_4)$ to determine that a calibration curve is valid for the given time period and, if the calibration curve is valid, to calculate the concentration of the targeted molecule M in the liquid sampling matrix by use of $R_{ave}(t_1)$, $R_{ave}(t_3)$ and the calibration curve and provide the concentration of the targeted molecule M in the liquid sampling matrix as an output;
   wherein the signal source emits radiation at a signal wavelength which is within a first absorption band of the targeted molecule M, the interference source emits radiation at an interference wavelength which is within a second absorption band of said at least one interfering molecule $M_J$, and the reference beam emits radiation at a reference wavelength which is neutral and is not within either the first absorption band or the second absorption band;
   wherein said at least one interfering molecule $M_J$ absorbs radiation at the signal wavelength; and
   wherein the signal source, the interference source and the reference source are each pulsed at a preselected frequency of at least N Hz which is sufficiently fast so that a given molecule of the targeted molecule M or said at least one interfering molecule $M_J$ will not pass in and out of the liquid sampling matrix within the preselected frequency.

2. The apparatus of claim 1, wherein the means for changing the imposed location of the pulsed beam does not change the physical location of either the pulsed beam or the detector.

3. The apparatus of claim 2, wherein the means for changing the imposed location of the pulsed beam uses an optical device to change the direction of the pulsed beam.

4. The apparatus of claim 3, wherein the means for changing the imposed location of the pulsed beam uses a piezo/electronic device to move the optical device.

5. The apparatus of claim 3, wherein the means for changing the imposed location of the pulsed beam uses an electronic device to move the optical device.

6. The apparatus of claim 3, wherein the means for changing the imposed location of the pulsed beam uses a magnetic device to move the optical device.

7. The apparatus of claim 3, wherein the means for changing the imposed location of the pulsed beam uses a mechanical device to move the optical device.

8. The apparatus of claim 1, wherein the means for changing the imposed location of the pulsed beam changes the physical location of the pulsed beam.

9. The apparatus of claim 1, wherein the means for changing the imposed location of the pulsed beam changes the physical location of the detector in tandem with the pulsed beam.

10. The apparatus of claim 1, wherein the targeted molecule M is glucose, said at least one interfering molecule $M_J$ is comprised of a plurality of interfering molecules contained in a body interstitial fluid and radiation emerging from the spot is collected by a lens onto the detector.

11. A process for determining a concentration of a targeted molecule M within a given time period in a non-homogenous liquid sampling matrix in which at least one interfering molecule $M_J$ coexists with the targeted molecule by use of a non-invasive apparatus, comprising the steps of:

pulsing infrared radiation from a signal source, an interference source and a reference source into a multiplexer and collimating radiation leaving the multiplexer into a pulsed beam which is directed at a scanning sample of three or more spots of the liquid sampling matrix;

detecting infrared radiation by a detector after it emerges from the scanning sample of three or more spots as a pulsed signal and reference channel output and a pulsed interference signal and reference channel output from the pulsed beam after it penetrates into the scanning sample of three or more spots;

using signal processing to obtain an average ratio value of $R_{ave}(t)$ for a first preselected period of time ("t") from the pulsed signal and reference channel output, where $R_{ave}(t)$=signal channel/reference channel output for the first preselected period of time;

using signal processing to obtain an average ratio value of $R_{Jave}(t_2)$ for a second preselected period of time ("$t_2$") from the pulsed interference and reference channel output, where $R_{Jave}(t_2)$=interference channel/reference channel output for the second preselected period of time;

determining a chosen calibration curve for the non-invasive apparatus;

using electronics to calculate the concentration of the targeted molecule M in the liquid sampling matrix by use of $R_{ave}(t)$ and the chosen calibration curve; and providing the concentration of the targeted molecule M in the liquid sampling matrix as an output from said electronics wherein the signal source emits radiation at a signal wavelength which is within a first absorption band of the targeted molecule M, the interference source emits radiation at an interference wavelength which is within a second absorption band of said at least one interfering molecule $M_J$, and the reference beam emits radiation at a reference wavelength which is neutral and is not within either the first absorption band or the second absorption band;

wherein said at least one interfering molecule $M_J$ absorbs radiation at the signal wavelength;

wherein the signal source, the interference source and the reference source are each pulsed at a preselected frequency of at least N Hz which is sufficiently fast so that a given molecule of the targeted molecule M or said at least one interfering molecule $M_J$ will not pass in and out of the liquid sampling matrix within the preselected frequency; and wherein the chosen calibration curve is obtained by the steps of:

using the non-invasive apparatus to obtain a set of calibration curves for a set of different known concentration samples wherein each of the set of calibration curves contains a plurality of assumed β values, wherein β is a parameter indicating the ratio of the absorption strength of interfering molecules measured respectively at the signal wavelength and the interference wavelength;

using the non-invasive apparatus to calculate the concentration of the targeted molecule M in a known concentration calibration sample by use of $R_{ave}(t)$ and determining a best calibration curve of the set of calibration curves which achieves a calculated concentration closest to a known concentration of the known calibration sample; and using the best calibration curve as the chosen calibration curve.

* * * * *